United States Patent [19]

Rosenzweig et al.

[11] Patent Number: 4,806,648
[45] Date of Patent: Feb. 21, 1989

[54] EFFICIENT SYNTHESIS OF CYCLIC CIS-VICINAL TERITIARY DIAMINES

[75] Inventors: Howard Rosenzweig, N. Massapequa, N.Y.; Gideon Fraenkel, Columbus, Ohio

[73] Assignee: Ohio State University Research Foundation, Columbus, Ohio

[21] Appl. No.: 943,663

[22] Filed: Dec. 18, 1986

[51] Int. Cl.$^4$ .......................................... C07D 401/08
[52] U.S. Cl. .................................... 546/191; 546/208; 546/229; 548/524; 548/569; 564/461
[58] Field of Search ..................... 546/208, 191, 229; 548/569, 524; 564/461

[56] References Cited

U.S. PATENT DOCUMENTS 4,680,410 7/1987 Wang ................................. 540/526

Primary Examiner—Robert T. Bond
Attorney, Agent, or Firm—Emch, Schaffer, Schaub & Porcello Co.

[57] ABSTRACT

The one aspect of this invention relates to a process for making cis-vicinal tertiary diamines of general formula:

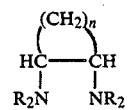

$n = 2-8$ wherein n is from 2-8, and $NR_{21}$ is selected from a group including N-piperidino, N-pyrrolidino, dialkylamino containing $C_1$–$C_{12}$ straight or branched alkyl groups optionally substituted by $C_3$–$C_7$ cycloalkyl groups. The process comprises the formation of a cyclic aminoenamine and the stereospecific catalytic hydrogenation of cyclic aminoenamine to a cis diamine. Another aspect of this invention involves the uses of cis-vicinal tertiary diamines as catalysts of organolithium initiated anionic polymerization of 1,3-dienes, as antineoplastic agents and as bacteriacides.

6 Claims, 2 Drawing Sheets

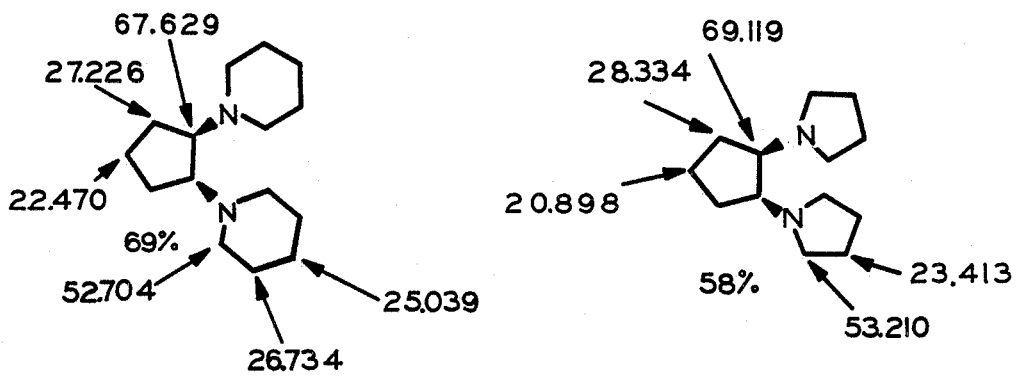
FIG. 3
FIG. 4
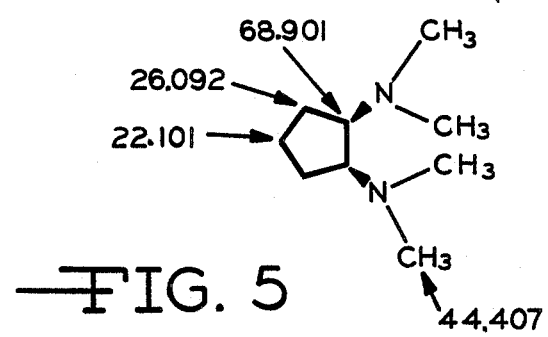
FIG. 5
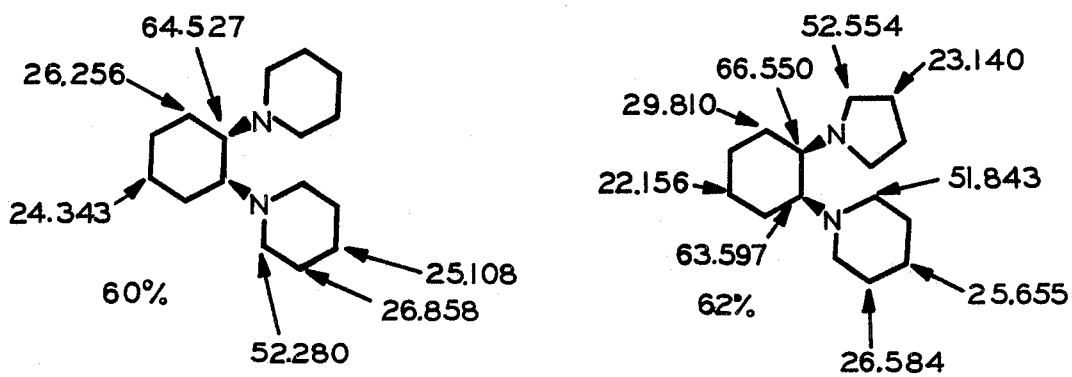
FIG. 6
FIG. 7

EFFICIENT SYNTHESIS OF CYCLIC CIS-VICINAL TERITIARY DIAMINES

BACKGROUND OF THE INVENTION

The present invention relates generally to the first efficient process for the manufacture of cyclic cis-vicinal tertiary diamines, compounds known to be extremely effective as drugs as well as possible catalysts for certain organometallic reactions.

Polyamines, including vicinal diamines, play a critical role in metabolism, controlling cell growth and cell division. The polyamines spermine and spermidine complex with DNA, RNA and t-RNA changing the conformations of these host molecules. Among diamines not found in living organisms, some are antineoplastic, for example 1,2 bis(N-3,5-diketopiperazenyl)-propane, whereas others are metastatic, bacteriacidyl or act as neurotoxins.

The most potent agent against testicular cancer is a platinum complex of cis-1,2-diaminocyclohexane. The effectiveness of this drug is believed to result from the cis arrangement of the amino groups.

Vicinal tertiary diamines accelerate the reactions of organolithium compounds, compared to just using monoamines.

Vicinal diamines exert significant chemotherapeutic effects and are often active as catalysts in simple organic reactions. The pharmacological and catalytic potential of these substances is significantly enhanced when the amino groups are oriented cis to one another.

Such compounds have not been extensively used in medicine because hitherto there has been no efficient method to make them. With the present invention it is now possible to efficiently synthesize cyclic cis-vicinal tertiary diamines.

Existing methods for synthesizing vicinal tertiary diamines are inefficient; most methods are not stereospecific and are unsuitable to be scaled up for commercial production. These existing methods include use of Curtius reactions, azide chemistry, metalloamination, imidoalkyl osmium and tosylimino selenium, reagents, respectively, and reductions of bis vicinal-nitro compounds, oximes, nitroso compounds and nitrile oxides. Another method based on cyanamino bromination of alkenes has been used to produce unsubstituted cis vicinal diamines. Recently a method which has had some success is the preparation of vicinal tertiary diamines via reductive animation of a 2-dialkylamino cyclic ketone.

So far applicants can determine, however, there are no prior art references or practices which comprises the catalytic reduction of cyclic aminoenamines to efficiently synthesize cyclic cis-vicinal tertiary diamines. The present invention therefore provides an improved method of synthesizing cyclic cis-vicinal tertiary diamines.

SUMMARY OF THE INVENTION

The one aspect of this invention relates to a process for making cis-vicinal tertiary diamines of general formula:

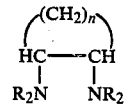

$n = 2-8$ wherein n is from 2–8, and $NR_2$ is selected from a group including N-piperidino, N-pyrrolidino, dialkylamino containing $C_1$–$C_{12}$ straight or branched alkyl groups, optionally substituted by $C_3$–$C_7$ cycloalkyl groups, such as, for example, dimethylamino, diethylamino, diisopropylamino and dibutylamino. The cyclic cis diamines can be made in a variety of sizes.

The process comprises the formation of a cyclic aminoenamine and the stereospecific catalytic hydrogenation of the cyclic aminoenamine to a cis diamine.

Another aspect of this application involves the uses of cis-vicinal tertiary diamines as catalysts of organolithium initiated anionic polymerization of 1,3-dienes, as anti-neoplastic agents and bacteriacides.

BRIEF DISCRIPTION OF THE FIGURES

FIG. 3 shows a structure of a diamine prepared together with $^{13}C$ NMR shifts and yields.

FIG. 4 shows a structure of a diamine prepared together with $^{13}C$ NMR shifts and yields.

FIG. 5 shows a structure of a diamine prepared together with $^{13}C$ NMR shifts and yields.

FIG. 6 shows a structure of a diamine prepared together with $^{13}C$ NMR shifts and yields.

FIG. 7 shows a structure of a diamine prepared together with $^{13}C$ NMR shifts and yields.

DESCRIPTION OF THE PREFERRED EMBODIMENT

Figure 1:
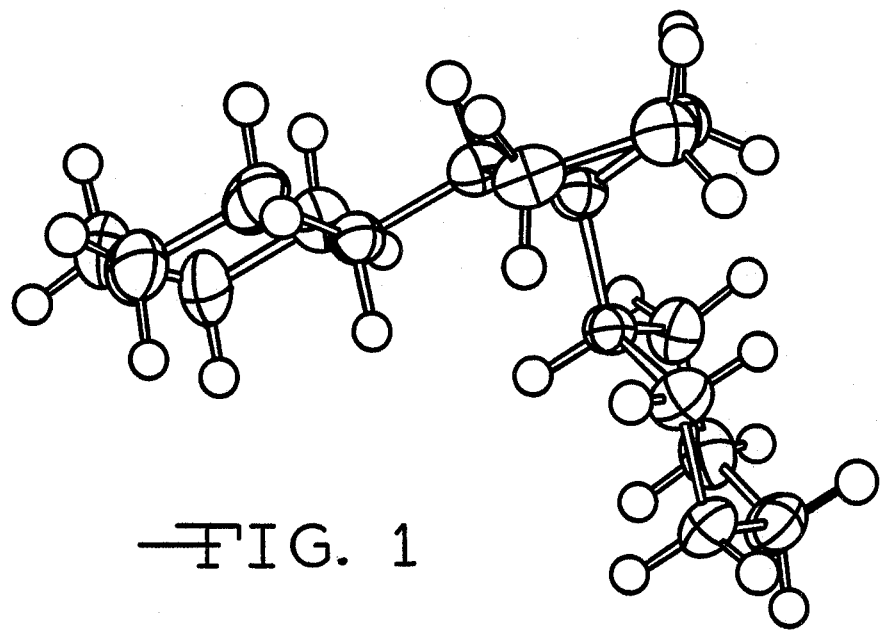
FIG. 1 is an ORTEP diagram of dipicrate of cis-1,2-dipiperidylcyclopentone, showing one picrate anion.

The present invention provides an improved and alternative process for the production of cis-vicinal tertiary diamines which process is less encumbered with side-reactions and is more efficient compared to currently used procedures. In particular, the process of the present invention comprises the catalytic reduction of a cyclic aminoenamine. This catalytic reduction proceeds from the unhindered side, giving cis-diamine, with none of the complications in work-up typically found in most other syntheses.

The invention thus provides a process for the preparation of compounds of the general formula 1:

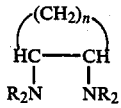

$n = 2-8$ wherein n is from 2–8 and the $R_2N$ substituent is selected from N-piperidino, N-pyrrolidino, dialkylamino containing $C_1$–$C_{12}$ straight or branched alkyl groups, optionally substituted by $C_3$–$C_7$ cycloalkyl groups, such as for example dimethylamino, diethylamino, diisopropylamino or dibutylamino.

According to a first example, a compound of general formula 1 may be prepared by converting a compound of formula 2, wherein n is from 2–8

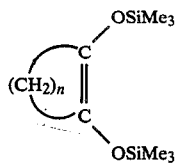

2 with methanol and $R_2NH$, where the $R_2N$ substituent is as described above, to give an amino ketone of the formula 3.

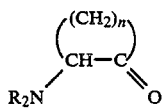

3

The aminoketone of the formula 3 is tranformed, using $R_2NH$ in benzene with an acid catalyst to an aminoenamine of the formula 4

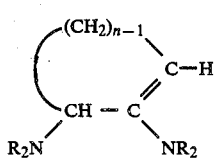

4 which undergoes clean quantitative hydrogenation to yield a cis diamine of the general formula 1.

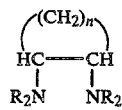

1 n = 2–8

According to another example, the hydroxyketone of the formula 5 is treated with benzene, $R_2NH$, and an acid catalyst to give the aminoenamine of the formula 4 directly.

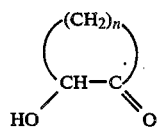

5

In a particular embodiment of this process the acyloin product 6 is smoothly converted to aminoketone 7 followed by transformation to aminoenamine 8. The latter, 8, undergoes clean quantitative hydrogenation, Pd(C), to yield the cis-diamine 9. Reactions involving the aminoenamine and the diamine compounds are carried out with rigorous exclusion of oxygen and water.

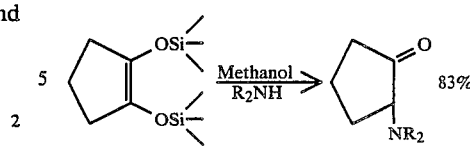

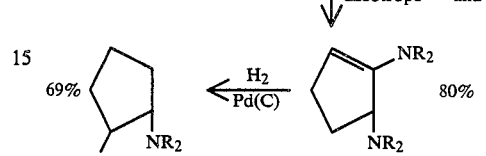

$R_2N$ = piperidyl

According to another example of the invention, the hydroxy ketone compound 10 is treated with benzene, a secondary amine, $R_2NH$, and an acid catalyst to give the aminoenamine 8 directly.

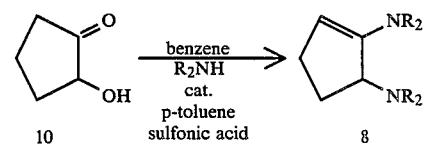

Figure 2:
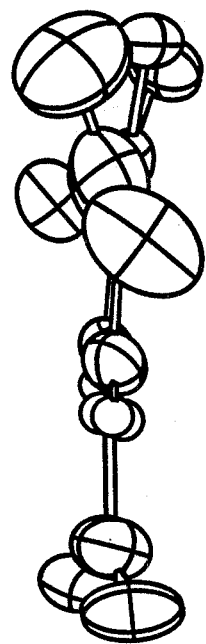
FIG. 2 is an ORTEP diagram of dipicrate of cis-1,2-dipiperidylcyclopentone, showing one diammonium cation.

The structure of various diamine compounds, their $^{13}CNMR$ shifts and yields, made using the above general process are shown in FIG. 2.

In a further example of the above process, the reductive alkylation of aminoenamine by Grignard reagent generates the quaternary substituted vicinal diamines as follows:

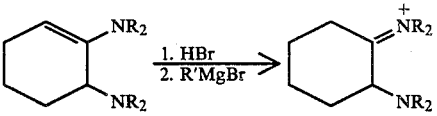

R' = ethyl
2-butyl
phenyl
enolate
anions
$R_2N$ as above

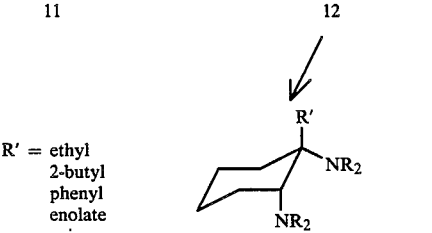

The following examples illustrate that with the catalytic reduction process of the present invention, cyclic cis-vicinal diamines are obtained in relatively high yields.

Carbon-13 NMR spectra were obtained using a Bruker WH-80 instrument. Proton NMR was carried out with Varian EM-360 and EM-390 equipment. All amines were purified by distillation from calcium hydride; all reactions were carried out with rigorous exclusion of oxygen, under an argon atmosphere. Air sensitive compounds were transferred by syringe whenever possible. A Hewlett Packard Model No. 5710A glass capillary gas chromatograph was used to monitor reaction progress.

EXAMPLE 1

2-N-Piperidinocyclohexanone (4)

A 100 ml Schlenk flask, equipped with two inlets, (top and side) bearing 2 mm straight bore stopcocks protected by serum caps, was flamed out in a current of dry argon and loaded by syringe with 17 ml dry methanol, piperidine (6.0 g, 0.07 mole) and then with the 1,2-bis(trimethylsiloxy)cyclohex-1-ene (9) (17.69 g, 0.069 mole). After stirring for 63 h, piperidine and methanol were removed by pumping, leaving a wet amorphous solid, of 2-hydroxycyclohexanone, which was dissolved in 35 ml benzene and reacted with piperidine (6.0 g, 0.07 mole) in an apparatus consisting of reaction flask, with reflux condensor connected above and to the side and a Dean Stark trap attached directly below the drop tip of the condensor. The reaction mixture was refluxed for four days, benzene removed at reduced pressure and the residue fractionated at high vacuum to yield 42% 2-N-piperidylcyclohexanone, 5.31 g; b.p. 55°-62°/0.18 Torr; and 41% 1,6-di-N-piperidylcyclohexene, 6.82 g; b.p. 90°-97°/0.15 Torr; yields based on starting material.

EXAMPLE 2

Amino-enamine Procedure, 1,5-di-N-piperidino-cyclopent-1-ene (8)

A 100 ml flask with stopcock side-arm was fitted with a standard Dean-Stark trap and attached condenser. A few crystals of p-toluene sulfonic acid were introduced. After the trap and condenser were attached, benzene (19 ml) was syringed into the flask followed by 2-N-piperidylcyclopentanone (8.99 g, 0.05 mole) and then distilled piperidine (4.8 g, 0.05 mole). Benzene was loaded into the Dean-Stark trap and the entire system filled with argon and kept under an argon atmosphere throughout the entire reaction and isolation-purification process. The reaction mixture was refluxed until the trap no longer accumulated water. Gas chromatography was also used to monitor product formation. Reflux typically took 48 hours. Then benzene was slowly removed using house-vacuum and the residue purified by vacuum distillation in a short path still, to yield 80% clear light yellow 1,5-di-N-piperidino-cyclopent-1-ene, 9.46 g; b.p. 100°-106°/0.54 Torr.

EXAMPLE 3

Cis-1,2-Dipiperidylcyclopentane (9)

A flamed Parr Jar, equipped with a #6 rubber (neoprene) stopper and septum, was flamed out under current of argon and loaded via syringe with 100 ml of ethyl acetate, followed by enamine, 1,5-di-N-piperidino-cyclopent-1-ene (4) (7.54 g, 0.032 mole) and finally 5% Pd(C) (0.75 g) was quickly introduced. After flushing a second time with argon, the system was attached to the Parr hydrogenator, pressured at 40 lbs. Hydrogenation took 12 minutes, however the system was left in contact with H₂ for 12 additional hours. The reaction mixture was filtered twice under argon, solvent removed by rotary evaporation and the residue washed out with 15 ml dry ether. After transfer via Pasteur pipette to a 25 ml flask, ether was removed by distillation (atmospheric pressure) and the residue vacuum distilled to yield 69% cis-1,2-dipiperidylcyclopentane, 5.25 g, b.p. 83°-87°/0.17 Torr. The cis structure was confirmed by X-ray crystallography of the diprIcate salt, as shown in the ORTEP diagram of FIG. 1.

We claim:

1. A process for preparing a cyclic cis-vicinal diamine compound of formula 1, wherein NR₂ is selected from the group including N-piperidino, N-pyrrolidino, dialkylamino containing C₁–C₁₂ straight or branched alkyl groups optionally substituted by C₃–C₇ cycloalkyl groups, and n is from 2-8

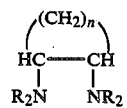

n = 2-8 which comprises:
(a) reacting a compound of formula 2,

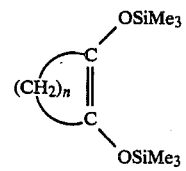

with methanol and R₂NH wherein the substituent R₂N— is selected from one of the following substituent groups: N-piperidino, N-pyrrolidino, dialkylamino containing C₁–C₁₂ straight or branched alkyl groups optionally substituted by C₃–C₇ cycloalkyl groups, whereby the 1,2-siloxycloalkene, 2, is converted to an aminoketone of formula 3,

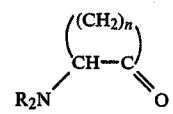

(b) reacting the compound of formula 3 in benzene with R₂NH and an acid catalyst, under Dean-Stark conditions, whereby a compound of formula 4 is obtained; and,

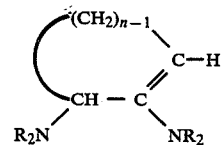

(c) reacting the compound of formula 4 with hydrogen and a catalyst whereby such compound of formula 1 is obtained.

2. The process of claim 1 for making the cyclic cis-vicinal diamine compound of formula 1 wherein NR₂ is a N-piperidino group.

3. The process of claim 1 for making the cyclic cis-vicinal diamine compound of formula 1 wherein NR₂ is a N-pyrrolidino group.

4. The process of claim 1 for making the cyclic cis-vicinal diamine compound of formula 1 wherein $NR_2$ is a dimethylamino group.

5. The process of claim 1 for making the cyclic cis-vicinal diamine compound of formula 1 wherein $NR_2$ is diethylamino group.

6. A process for preparing a compound of formula 1,

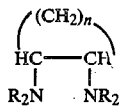

$n = 2-8$ which comprises:

(a) reacting a cyclic 2-hydroxyketone compound of formula 5

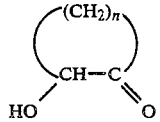

with a secondary amine, $R_2NH$ wherein the substituent $R_2N$— is selected from one of the following substituent groups: N-piperidino, N-pyrrolidino, dialkylamino containing $C_1$–$C_{12}$ straight or branched alkyl groups optionally substituted by $C_3$–$C_7$ cycloalkyl groups, in benzene with an acid catalyst, to give the aminoenamine compound of the formula 4; and, (b) and, reacting the compound of formula 4 with hydrogen and a catalyst whereby such compound of formula 1 is obtained.

* * * * *